(12) United States Patent
Su et al.

(10) Patent No.: US 11,345,888 B2
(45) Date of Patent: May 31, 2022

(54) METHOD AND PHARMACEUTICAL COMPOSITION FOR CONTINUOUSLY MAINTAINING GROWTH OF A MOTOR NEURON PROGENITOR CELL

(71) Applicant: TAIWAN MITOCHONDRION APPLIED TECHNOLOGY, Taiwan (TW)

(72) Inventors: Hong-Lin Su, Taichung (TW); Hung-Chuan Pan, Taichung (TW); Hsiu-Chin Lee, Taichung (TW); Chun-Wei Chuang, Taichung (TW); Shinn-Zong Lin, Taichung (TW); Horng-Jyh Harn, Taichung (TW)

(73) Assignee: TAIWAN MITOCHONDRION APPLIED TECHNOLOGY, Zhubei (TW)

( * ) Notice: Subject to any disclaimer, the term of this patent is extended or adjusted under 35 U.S.C. 154(b) by 0 days.

(21) Appl. No.: 14/929,017

(22) Filed: Oct. 30, 2015

(65) Prior Publication Data

US 2016/0122710 A1  May 5, 2016

(30) Foreign Application Priority Data

Nov. 4, 2014 (TW) ................................ 103138245

(51) Int. Cl.
*A61K 35/30* (2015.01)
*C12N 5/0793* (2010.01)

(52) U.S. Cl.
CPC ............ *C12N 5/0619* (2013.01); *A61K 35/30* (2013.01); *C12N 2502/083* (2013.01)

(58) Field of Classification Search
None
See application file for complete search history.

(56) References Cited

PUBLICATIONS

Okada et al. (Stem cells 26: 3086-3098, 2008).*
Sethi et al. (Stem Cell Rev 10: 772-785, 2014).*
Zhao et al (Jiepou Xuebao 39: 40-44, 2008—abstract only).*
Protocol online <http://www.protocol-online.org/biology-forums-2/posts/12918.html>, downloaded on Oct. 12, 2018.*
Hoffman et al. Nat Biotechnol. 23:699-708, 2005).*
Lundqvist et al (Toxicol in vitro 27: 1565-1569, 2013).*
Schuldiner et al. (PNAS, 97:11307-11312, 2000).*
Yan et al (Tissue Eng 20: 340-354, 2014).*
Kozubenko N, Tumovcova K, Kapcalova M, Butenko O, Anderova M, et al. (2010) Analysis of in vitro and in vivo characteristics of human embryonic stem cell-derived neural precursors. Cell Transplant 19: 471-486.
Mandai M, Ikeda H, Jin ZB, Iseki K, Ishigami C, et al. (2010) Use of lectins to enrich mouse ES-derived retinal progenitor cells for the purpose of transplantation therapy. Cell Transplant 19: 9-19.
Boddington SE, Henning TD, Jha P, Schlieve CR, Mandrussow L, et al. (2010) Labeling human embryonic stem cell-derived cardiomyocytes with indocyanine green for noninvasive tracking with optical imaging: an FDA-compatible alternative to firefly luciferase. Cell Transplant 19: 55-65.
Muguruma K, Sasai Y (2012) In vitro recapitulation of neural development using embryonic stem cells: from neurogenesis to histogenesis. Dev Growth Differ 54: 349-357.
Willerth SM (2011) Neural tissue engineering using embryonic and induced pluripotent stem cells. Stem Cell Res Ther 2: 17.
Lopez-Gonzalez R, Kunckles P, Velasco I (2009) Transient recovery in a rat model of familial amyotrophic lateral sclerosis after transplantation of motor neurons derived from mouse embryonic stem cells. Cell Transplant 18: 1171-1181.
Harper JM, Krishnan C, Darman JS, Deshpande DM, Peck S, et al. (2004) Axonal growth of embryonic stem cell-derived motoneurons in vitro and in motoneuron-injured adult rats. Proc Natl Acad Sci U S A 101: 7123-7128.
Chiba S, Iwasaki Y, Sekino H, Suzuki N (2003) Transplantation of motoneuron-enriched neural cells derived from mouse embryonic stem cells improves motor function of hemiplegic mice. Cell Transplant 12: 457-468.
Lopez-Gonzalez R, Velasco I (2012) Therapeutic potential of motor neurons differentiated from embryonic stem cells and induced pluripotent stem cells. Arch Med Res 43: 1-10.
Chipman PH, Toma JS, Rafuse VF (2012) Generation of motor neurons from pluripotent stem cells. Prog Brain Res 201: 313-331.
Jessell TM, Surmeli G, Kelly JS (2011) Motor neurons and the sense of place. Neuron 72: 419-424.
Thonhoff JR, Ojeda L, Wu P (2009) Stem cell-derived motor neurons: applications and challenges in amyotrophic lateral sclerosis. Curr Stem Cell Res Ther 4: 178-199.
Wu CY, Whye D, Mason RW, Wang W (2012) Efficient differentiation of mouse embryonic stem cells into motor neurons. J Vis Exp: e3813.
Takazawa T, Croft GF, Amoroso MW, Studer L, Wichterle H, et al. (2012) Maturation of spinal motor neurons derived from human embryonic stem cells. PLoS One 7: e40154.

(Continued)

*Primary Examiner* — Gregory S Emch
*Assistant Examiner* — Aditi Dutt
(74) *Attorney, Agent, or Firm* — Muncy, Geissler, Olds & Lowe, P.C.

(57) ABSTRACT

This present invention provides a method for continuously maintaining growth of a motor neuron progenitor cell and a pharmaceutical composition. Wherein, the method for continuously maintaining growth of a motor neuron progenitor cell is to culture the motor neuron progenitor cell in an environment which is constructed by the olfactory ensheathing cells to make the motor neuron progenitor cell sustain the ability to self-replicate and to be induced for differentiating into mature neuron, and therefore to elaborate the effect to protect the motor neuron. The motor neuron progenitor cell produced from the method disclosed in this present invention can be an effective ingredient of the pharmaceutical composition for treating related diseases of damaged motor neuron.

4 Claims, 13 Drawing Sheets
(13 of 13 Drawing Sheet(s) Filed in Color)

(56) References Cited

PUBLICATIONS

Wada T, Honda M, Minami I, Tooi N, Amagai Y, et al. (2009) Highly efficient differentiation and enrichment of spinal motor neurons derived from human and monkey embryonic stem cells. PLoS One 4: e6722.

Wu SM, Tan KS, Chen H, Beh TT, Yeo HC, et al. (2012) Enhanced production of neuroprogenitors, dopaminergic neurons, and identification of target genes by overexpression of sonic hedgehog in human embryonic stem cells. Stem Cells Dev 21: 729-741.

Oh S, Huang X, Liu J, Litingtung Y, Chiang C (2009) Shh and Gli3 activities are required for timely generation of motor neuron progenitors. Dev Biol 331: 261-269.

Ruiz i Altaba A (1998) Combinatorial Gli gene function in floor plate and neuronal inductions by Sonic hedgehog. Development 125: 2203-2212.

Raimondi A, Mangolini A, Rizzardini M, Tartari S, Massari S, et al. (2006) Cell culture models to investigate the selective vulnerability of motoneuronal mitochondria to familial ALS-linked G93ASOD1. Eur J Neurosci 24: 387-399.

Cashman NR, Durham HD, Blusztajn JK, Oda K, Tabira T, et al. (1992) Neuroblastoma x spinal cord (NSC) hybrid cell lines resemble developing motor neurons. Dev Dyn 194: 209-221.

Raisman G, Li Y (2007) Repair of neural pathways by olfactory ensheathing cells. Nat Rev Neurosci 8: 312-319.

Miles GB, Yohn DC, Wichterie H, Jessell TM, Rafuse VF, et al. (2004) Functional properties of motoneurons derived from mouse embryonic stem cells. J Neurosci 24: 7848-7858.

Wichterle H, Lieberam I, Porter JA, Jessell TM (2002) Directed differentiation of embryonic stem cells into motor neurons. Cell 110: 385-397.

Arber S, Han B, Mendelsohn M, Smith M, Jessell TM, et al. (1999) Requirement for the homeobox gene Hb9 in the consolidation of motor neuron identity. Neuron 23: 659-674.

Pan HC, Wu YT, Shen SC, Wang CC, Tsai MS, et al. (2011) Characterization of axon formation in the embryonic stem cell-derived motoneuron. Cell Transplant 20: 493-502.

Cheng FC, Sheu ML, Su HL, Chen YJ, Chen CJ, et al. (2012) The effect of exercise on mobilization of hematopoietic progenitor cells involved in the repair of sciatic nerve crush injury. J Neurosurg.

Cheng FC, Tai MH, Sheu ML, Chen CJ, Yang DY, et al. (2010) Enhancement of regeneration with glia cell line-derived neurotrophic factor-transduced human amniotic fluid mesenchymal stem cells after sciatic nerve crush injury. J Neurosurg 112: 868-879.

Yang DY, Sheu ML, Su HL, Cheng FC, Chen YJ, et al. (2012) Dual regeneration of muscle and nerve by intravenous administration of human amniotic fluid-derived mesenchymal stem cells regulated by stromal cell-derived factor-1alpha in a sciatic nerve injury model. J Neurosurg 116: 1357-1367.

Soundararajan P, Miles GB, Rubin LL, Brownstone RM, Rafuse VF (2006) Motoneurons derived from embryonic stem cells express transcription factors and develop phenotypes characteristic of medial motor col. neurons. J Neurosci 26: 3256-3268.

Watanabe K, Kamiya D, Nishiyama A, Katayama T, Nozaki S, et al. (2005) Directed differentiation of telencephalic precursors from embryonic stem cells. Nat Neurosci 8: 288-296.

Ying QL, Stavridis M, Griffiths D, Li M, Smith A (2003) Conversion of embryonic stem cells into neuroectodermal precursors in adherent monoculture. Nat Biotechnol 21: 183-186.

Kawasaki H, Mizuseki K, Nishikawa S, Kaneko S, Kuwana Y, et al. (2000) Induction of midbrain dopaminergic neurons from ES cells by stromal cell-derived inducing activity. Neuron 28: 31-40.

Wang Xiu-jiao et. al, Proliferation and differentiation from neural stem cells into neurons following coculture with olfactory ensheathing cells, Journal of Clinical Rehabilitative Tissue engineering Research, Oct. 1, 2010, vol. 14, No. 40, p. 7501-504.

Yin Guodong et. al, Recovery of adult rat spinal cord injury by co-transplant of human olfactory ensheathing cells and neuron stem cells, Journal of Clinical Rehabilitative Medicine, Aug. 2006, vol. 21, No. 8, p. 680-719.

Tang Zhou-ping et. al, Effects of OECs on the proliferation and differentiation of NSCs, Chin J Exp. Surg., Sep. 2005, vol. 22, No. 9, p. 1123-1124.

Salehi M et. al, Repair of spinal cory injury by co-transplantation of embryonic stem cell-derived motor neuron and olfactory ensheathing cell, Iran Biomed J. Jul. 2009;13(3):125-35.

* cited by examiner

METHOD AND PHARMACEUTICAL COMPOSITION FOR CONTINUOUSLY MAINTAINING GROWTH OF A MOTOR NEURON PROGENITOR CELL

The current application claims a foreign priority to application number 103138245 filed on Nov. 4, 2014 in Taiwan.

BACKGROUND OF THE INVENTION

1. Field of the Invention

This invention relates to a method for maintaining growth of a neural stem cell, specially relates to a method and a pharmaceutical composition for continuously maintaining growth of a motor neuron progenitor cell.

2. Description of the Related Art

Pluripotent embryonic stem cells can be a kind of sources to produce required nerve cells, so it is the most potential candidate for the cell replacement therapy (Kozubenko N et al., 2010; Mandai M et al., 2010; Boddington S E et al., 2010). The general differentiation protocols for the ESCs sequentially apply neural induction factors and regional patterning factors to steer cell fate conversion, recapitulating the embryonic signals at the proceeding stages of neural development. (Muguruma K et al., 2012; Willerth S M, 2011). For example, primitive neural progenitor cells can be produced by the BMP-inhibitors and further directed to become spinal cord motor neurons by treating sonic hedgehog (Shh) and retinoic acid (RA). Accumulative evidence indicates that molecule profiles of ESC-derived neural cells are similar to those of embryonic neurons and particularly, the ESC-derived cells generally exhibit normal physiological functions. Engrafting ESC-derived neurons can successfully restore motor activities and behavior performance in disease-modeling animals, particularly when the engrafted neurons have a high rate of survival. (Lopez-Gonzalez R et al., 2009; Harper J M et al., 2004; Chiba S et al., 2003).

Motor neurons of the spinal cord and brainstem have been extensively explored as a distinct neuronal population, due to their large size, accessible peripheral projection to muscle, and selective involvement in human motor neuron diseases. (Lopez-Gonzalez R et al., 2012; Chipman P H et al., 2012; Jessell T M et al., 2011; Thonhoff J R et al., 2009). Although plural lineage-specific transcription factors of developing motor neuron have been found (Chipman P H et al., 2012; Wu C Y et al., 2012; Takazawa T et al., 2012; Wada T et al., 2009), there is almost no fundamental molecular research on the self-replication and maintenance of motor neuron group in compare with the neural stem cell group aside of the ventricles of the brain and hippocampus. Genetically modified mice revealed that Shh and its downstream Gli pathway are critical for the growth of motor neuron precursors (Wu S M et al., 2012; Oh S et al., 2009; Ruiz i Altaba A, 1998). Whether other secretory factors are required for the expansion of motor neuron pool are largely unknown. Besides, the low yields and low purity of motor neuron preparation limited the intensively studies of the proliferation. Although immortalized hybrid motor neuron clones, generated by the fusion of spinal cord neurons with mouse N18 neuroblastoma, were established (Raimondi A et al., 2006; Cashman N R et al., 1992), these cells are multi-nuclear and genetically abnormal. In addition, these hybrid cells are constitutively proliferative and do not show classical motor neuron morphology with a long and thin axon configuration.

Olfactory ensheathing cells (OECs), similar to the Schwann cell in the peripheral nervous system, are glia cells ensheathing the olfactory nerve fibers (Mackay-Sim A et al., 2011; Su Z et al., 2010; Raisman G et al., 2007). The OECs can be identified by expression of the glial fibrillary acidic protein (GFAP), s100, p75 and nestin intermediate filaments. When the OECs were co-cultured with neural stem cells, it can stimulate the differentiation of neural stem cells and the formation of neurites, but without inducing the growth and replication of neural stem cells.

Stem cell transplantation can be an effective treatment for neurodegenerative diseases and central nervous system diseases. Specifically speaking, the stem cell transplantation is to deliver stem cells into or nearby the damaged part of central nervous system to regenerate damaged neural cells of central nervous system. Recent studies have proved that transplantation of the OECs or neural progenitor cells shown positive results for the functional improvement of brain-damaged experimental rodents, including the animals having amyotrophic lateral sclerosis (ALS) and spinal cord injury (Mackay-Sim A et al., 2011). However, the experiment durations of the recent studies were generally within few months, and the observed effects of lesion amelioration were usually transient. This short-term therapeutic effect is tightly related to the low cell number of survived transplanted cells. Factors contributing to the low surviving rate of engrafted cells include the local inflammation and rejection, the inability of these cells for host tissue integration and improper environmental matrix for the survival of engrafted cells. Therefore, the low survive rate of the transplanted cells cause discontinuous of the effect of treatment.

SUMMARY OF THE INVENTION

The major propose of this present invention is to provide a method for continuously maintaining growth of a motor neuron progenitor cell. It comprises that culturing the motor neuron progenitor cell under a culture condition constructed by olfactory ensheathing cells (OECs) to make the motor neuron progenitor cell maintain the abilities of self-replication and differentiation to a mature motor neuron cell. The method of this invention can effectively protect the motor neurons.

Further another purpose of this present invention is to provide a pharmaceutical composition, which comprises an effective dosage of the motor neuron progenitor cells and at least one pharmaceutical acceptable carrier. By administrating the pharmaceutical composition to a subject having motor neuron damaged related disease such as stroke, spinal damage, neurodegenerative diseases, it can rebuild the nervous function of the subject and improve the effect of growth of motor neuron.

In order to achieve these foresaid purposes, one embodiment of this present invention discloses a method for continuously maintaining growth of a motor neuron progenitor cell, which comprises culturing a motor neuron progenitor cell under a culture condition constructed by an olfactory ensheathing cell to grow, wherein the culture condition makes the motor neuron progenitor cell maintain the ability to self-replicate and to differentiate to a mature motor neuron cell.

Preferably, the culture condition is a culture media with the olfactory ensheathing cell.

In one embodiment, the motor neuron progenitor cell is cultured in low-density.

In another embodiment, at least one of the motor neuron progenitor cell is seeded on the olfactory ensheathing cell.

Preferably, the culture condition is a culture media by pretreatment with the olfactory ensheathing cell, wherein the motor neuron progenitor cell is cultured in high-density.

By the method disclosed in this present invention, the motor neuron progenitor cell is continuously proliferating over 10 generations in the culture condition, and the single motor neuron progenitor cell can be grown into a colony.

In one embodiment of this present invention discloses a pharmaceutical composition. It comprises an effective dosage of the motor neuron progenitor cells and at least a pharmaceutical acceptable carrier, wherein the motor neuron progenitor cells were pre-treated under a culture condition constructed by an olfactory ensheathing cell.

Preferably, the motor neuron progenitor cells were pre-treated by a culture media with an olfactory ensheathing cell.

Preferably, the motor neuron progenitor cells were pre-treated by an OEC-free culture media which was pre-treated with the olfactory ensheathing cells.

Preferably, the pharmaceutical composition further comprises an olfactory ensheathing cell.

Preferably, the motor neuron progenitor cells and the olfactory ensheathing cells were pre-treated with equal ratio.

The method disclosed in this present invention for treating motor neural disease comprises administrating an effective dosage of the foresaid pharmaceutical composition to a subject.

Preferably, the disease can be stroke, spinal damage, neurodegenerative disease, amyotrophic lateral sclerosis or any disease having dying motor neuron.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

DETAILED DESCRIPTION OF THE INVENTION

Figure 1A:
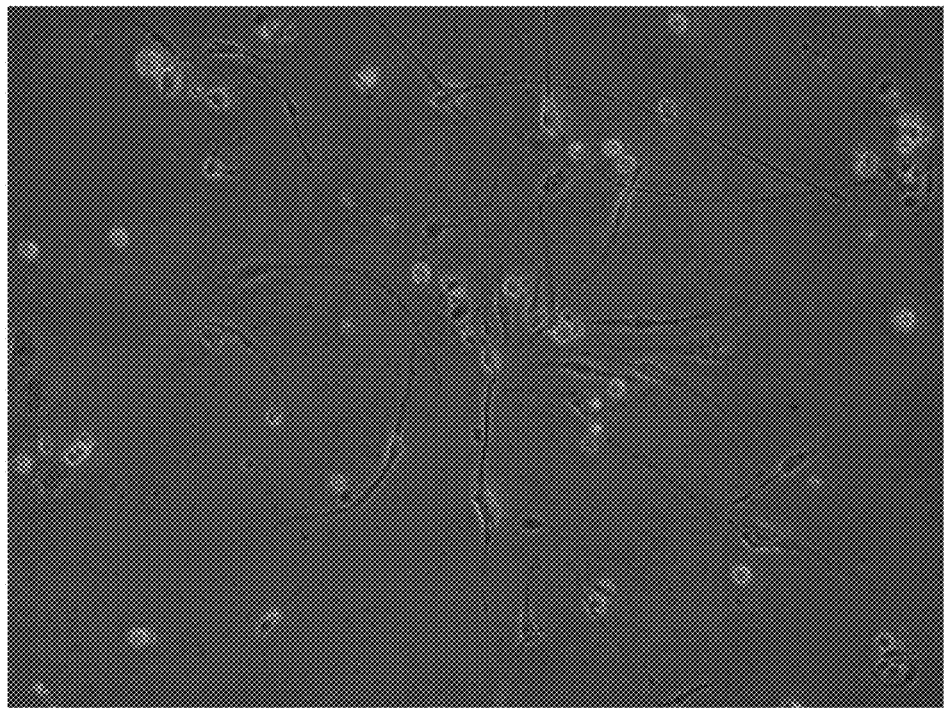
FIG. 1A shows the cell morphology of the cultured OECs on day 4.

The meaning of the technological and scientific terms disclosed in the specification and claims of this present invention is the same as the understanding from a person skilled in the art of this present invention and having general knowledge besides other definition. The content of this present invention is the first priority of explanation if there are contraries.

The "HB9::GFP embryonic stem cell" is a undifferentiated embryonic stem cell having a foreign gene which has the promoter of HB9 gene and the green fluorescent protein (GFP). The expression of the GFP in HB9::GFP embryonic stem cell was only detected in postmitotic motoneurons.

The "HB9::GFP$^+$ cell" is the motor neuron progenitor cell or mature motor neuron derived from embryonic stem cell and having green fluorescence. The expression of the GFP is regulated by HB9, the specific promoter of motor neuron (Miles G B et al., 2004; Wichterle H et al., 2002). HB9 is a specific transcription factor of a motor neuron (Arber S et al., 1999). Therefore, the expression of the GFP can be detected in motor neuron (Miles G B et al., 2004; Soundararajan P et al., 2006). In an example of this present invention, the HB9::GFP$^+$ cell is used to understand the effect of proliferation on the OECs and to quantify the proliferation ability of the motor neuron co-cultured with the OECs.

The "effective amount" means the amount of compound or active ingredient to generate specific effect which can be shown as the weight percentage in a composition. It can be understood by the person skilled in the art of this present invention and having general knowledge that the effective dosage will be different because of the administrating pathway which is trying to induce specific effect. Generally speaking, the amount of the active ingredient or compound in the composition can take about 1% to about 100% of weight, better will be about 30% to about 100% of weight.

The "pharmaceutical acceptable carrier" includes any standard carrier has been used in pharmaceutical product. According to the type of the composition, the carrier can be solid, semisolid or liquid. For example, the carrier includes but limited to gelatin, emulsifier, hydrocarbon mixtures, water, glycerol, saline, lanolin, paraffin wax, beeswax, polydimethylsiloxane or ethanol.

The "pharmaceutical composition" includes an effective dosage of compound or active ingredient which is necessary to produce specific effect, and at least a carrier. It can be understood by the person skilled in the art of this present invention and having general knowledge that the type of composition can be different according to the administration pathway such as tablet, powder or injection. The carrier also can be solid, semisolid or liquid according to the type of the composition.

The "administrate" means the way to deliver an object to a specific region, cell, target or the contact pathway to the subject. General speaking, the administration pathway includes, but not limit to, oral, smear, spray, inhale or inject.

The "a" or "an" is defined as one or as more than one.

Hereinafter, there are several examples for further illustrating the effect of this present invention. But these examples are only for explanation. Any words mentioned do not tend to limit the scope and meaning of the specification and claims of this present invention.

One thing needs to be clarified in advanced is that the following examples of animal test were all approved by the ethic committee of Taichung Veterans General Hospital. And all culture medium and addiction ingredients were obtained from Invitrogen in the following examples if there were not any further explanations.

Example 1

Maintaining and Differentiating Embryonic Stem Cells

The HB9 transgene embryonic stem cells (hereinafter "HB9::GFP embryonic stem cells"), from Columbia University in the United Stated, was derived from HB9::GFP transgenic mice. It can differentiate into motor neuron progenitor cells and mature motor neuron (hereinafter "HB9::GFP$^+$ cells").

The HB9::GFP embryonic stem cells were maintained on mitomycin C-treated mouse embryonic fibroblast cells in high-glucose DMEM, supplemented with 15% fetal bovine serum, 2 mM glutamine, 0.1 mM nonessential amino acids, 1 mM pyruvate, 0.1 mM 2-mercaptoethanol (Sigma-Aldrich), and 1000 U/ml leukemia inhibitory factor (Chemicon).

The detail of the neural differentiation method is well-known by the person skilled in the art of this present invention and having general knowledge according to prior art. It includes serum-free embryoid-body-like (SFEB)(Watanabe K et al., 2005), neurobasal/N2B27 culture medium (Ying Q L et al, 2003) and stroma cell-derived inducing activity methods (SDIA methods)(Kawasaki H et al., 2000).

The day on which ES cells were seeded to differentiate is defined as differentiation day 0. 0.1 μM Retinoic acid (RA; Sigma-Aldrich) was added into the differentiation medium from day 3 to day 5. Exogenous sonic hedgehog (Shh; 200 μM, R&D Systems) and purmorphamine (PU; 0.2 μM, Tocris) were added and replaced every other day during day 5 to day 7.

Example 2

Culturing and Purifying the OECs

Figure 1B:
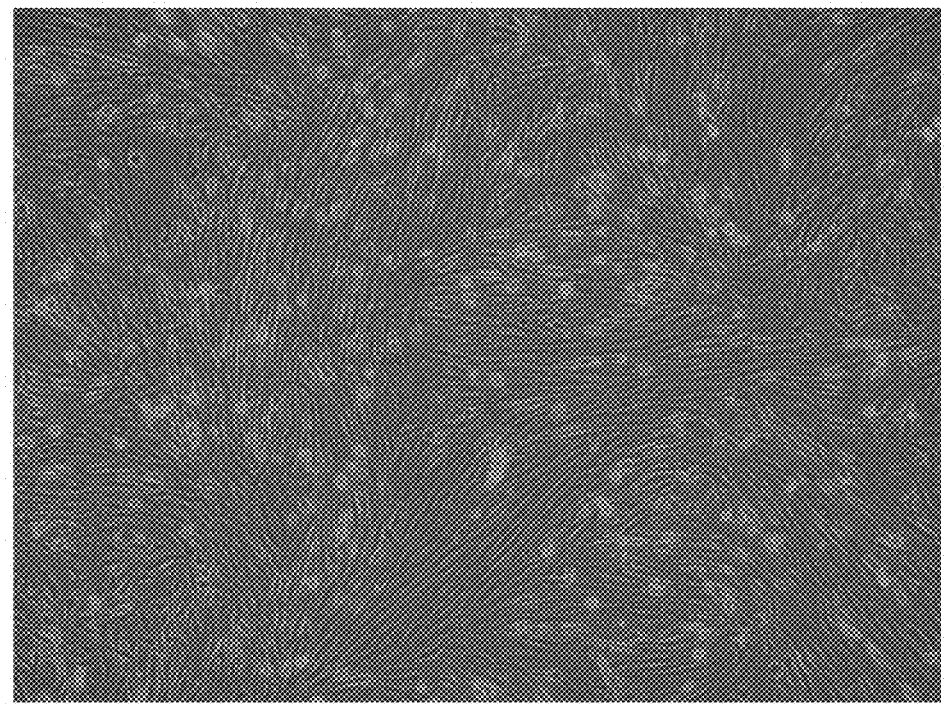
FIG. 1B shows the cell morphology of the cultured OECs on day 7.

Weight about 250-300 kilograms SD rat (Sprague-Dawley Rat) was taken to separate the OECs from olfactory mucosa (OM) or olfactory bulb (OB) of the rat. The OECs were continuously cultured in selective media. The cell morphology on day 4 and 7 were observed under the microscope, and the results shown as FIG. 1. From FIG. 1, the morphology of the OECs showed a typical spindle shape.

The OECs separated from olfactory mucosa and olfactory bulb and baby hamster kidney fibroblast cells (BHK-21 cell) were further analyzed by immunocytochemistry method. The cells were fixed by 4% cold paraformaldehyde and permeabilized with 0.3% Triton-X 100. Immunocytochemistry was performed using the following primary antibodies: S100 and p75. Then the cells were washed twice with 0.1% Tween-20 in phosphate buffered saline (PBS) to remove the first antibody. Appropriate fluorescence-tagged secondary antibodies (all from Jackson ImmunoResearch) were used for visualization. The 4',6-diamidino-2-phenylindole (DAPI) was used for nuclear counter-staining. Images of immunostaining were captured using an upright microscope (Nikon ECLIPSE 801) or confocal microscope (LSM510 Meta, Zeiss). The results were shown as FIG. 2, wherein the red color in the upper row was the result of staining by p75 antibody, the red color in the middle row was the result of immunostaining by S100 antibody, the blue color in this figure was the result of staining by DAPI.

The OECs were stained by p75 antibody and analyzed by fluorescence activated cell sorter (FACS). Then, the dead cells were eliminated by trypan blue. The cell number of the OECs was analyzed and the growth curve was recorded. The results were shown as FIG. 3.

Figure 2:
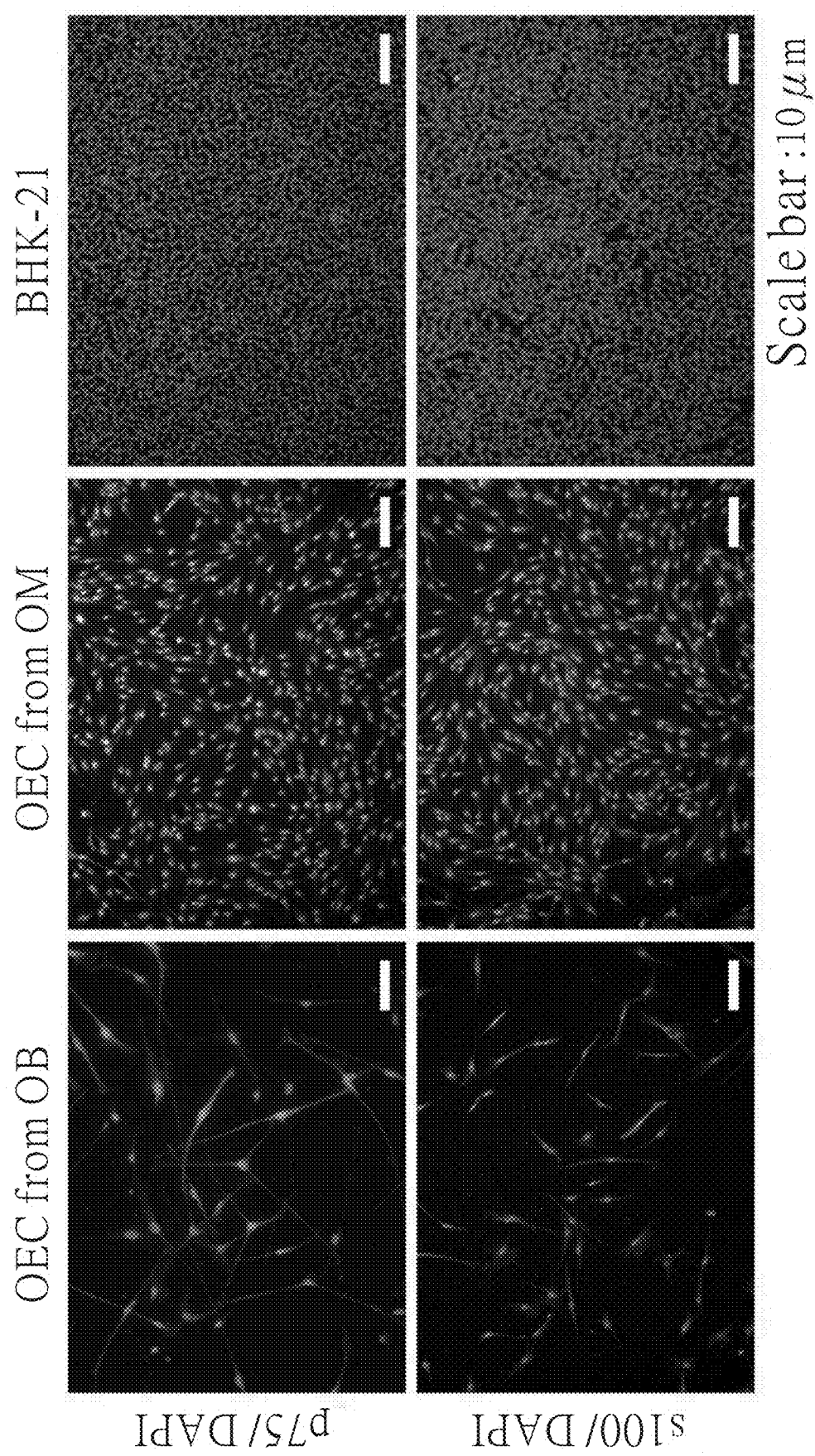
FIG. 2 shows the expressions of typical OEC markers, such as S100 and p75 proteins from the OECs from the olfactory bulb (OB) the OECs from the olfactory mucosa (OM) and BHK-21 cells (baby hamster kidney fibroblast cells) by immunocytostaining.
Figure 3A:
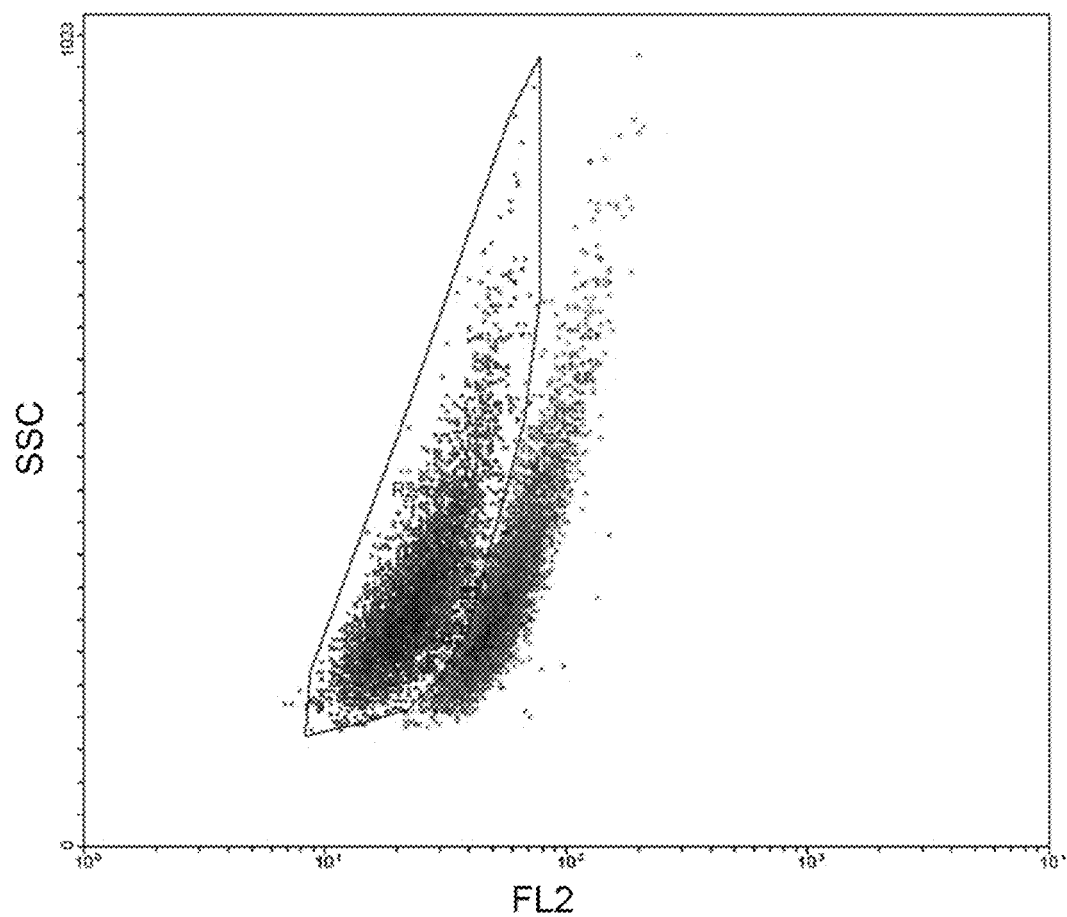
FIG. 3A shows the OECs stained with p75 antibody and analyzed by the fluorescence activating cell sorting technology, wherein the red color indicates the p75 antibody stained OECs and the blue color indicates the cells without staining.
Figure 3B:
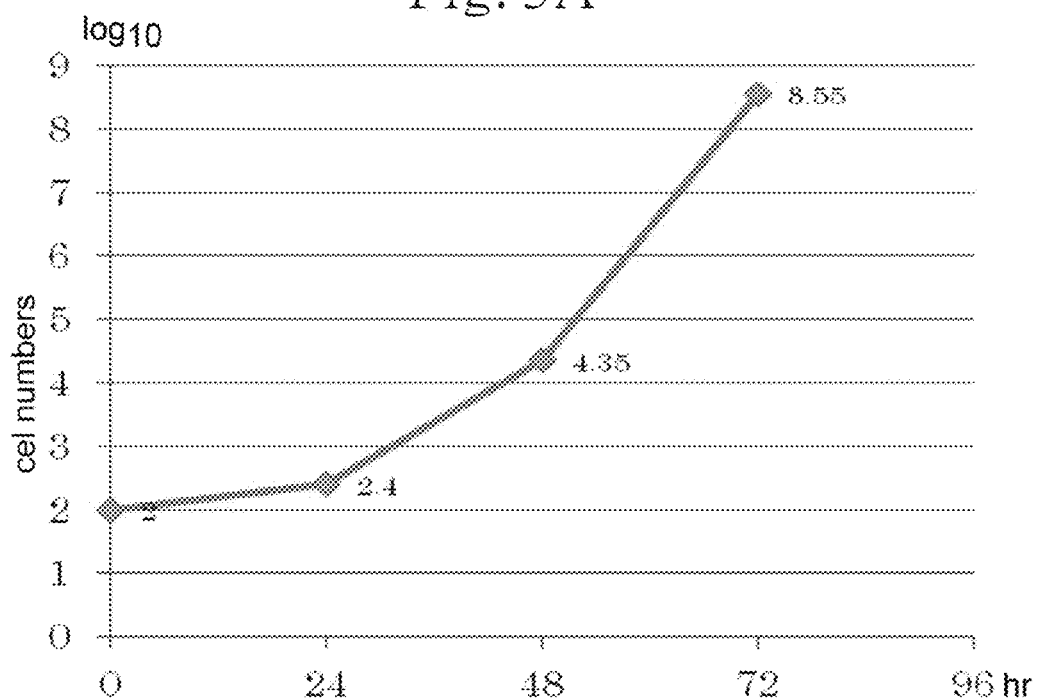
FIG. 3B shows the growth curve of the OECs.

The result from FIG. 2 shows that almost all cultured OECs expressed the OECs marker such as p75, S100, but the fibroblast of baby hamster did not express p75 and S100 antigen. It proved that this culture method can produce highly purity of the OECs. Furthermore, the result of FIG. 3 shows that most of the OECs can be stained by p75 antibody (red part in the figure) in compared with those OECs cannot be stained (blue part in the figure). According to FIG. 3, the OECs were proliferative and showed a double time around 28-32 hours.

Example 3

Figure 4:
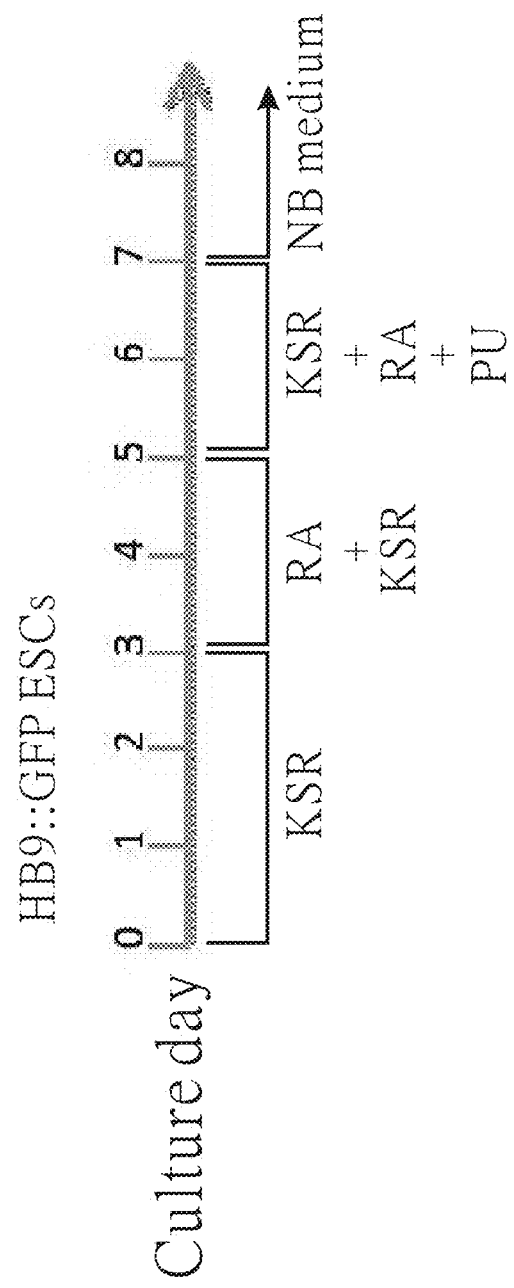
FIG. 4 shows the flow chart of the HB9::GFP embryonic stem cells co-cultured with the mouse preosteoblast cell line PA6.

Co-Culturing the Mouse Preosteoblast Cell Line and Motor Neuron Derived from Embryonic Stem Cell Please see FIG. 4. The mouse HB9::GFP embryonic stem cells from the example 1 co-cultured with the mouse preosteoblast cell line (PA6 cells) according to the following protocol revealed in prior reference (Pan H C et al., 2011): 10% knockout serum replacement (KSR) was used in the culture media at day 0-3, the KSR culture media containing RA was used at day 3-5, the neurobasal media (NB, Invitrogen) containing RA and PU was used for co-culturing at day 5-7. Then, the HB9::GFP cells were cultured on NB culture media till day 8 as FIG. 5.

Figure 5:
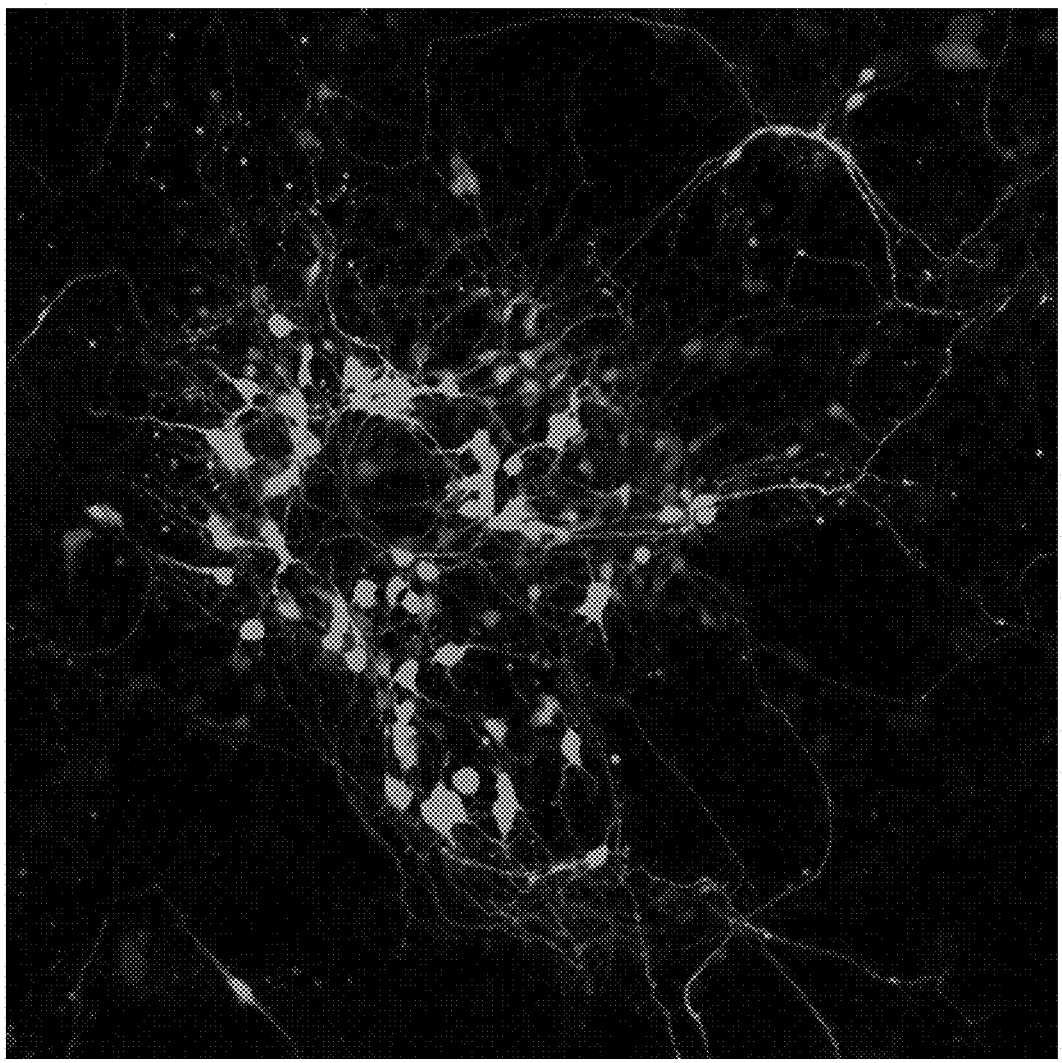
FIG. 5 shows the differentiating HB9::GFP+ cells on PA6 cells on day 8.

FIG. 5 shows that the HB9::GFP$^+$ cells co-cultured with the mouse preosteoblast cell line PA6 had differentiated into motor neuron which can express GFP and show classical unipolar morphology of motor neuron. From former researches of the inventor of this present invention, it could be known that the mESC-derived motor neurons also expressed the choline acetyltransferase and the specific protein, MND2 (Pan H C et al., 2011). Accordingly, it can be understood that the HB9::GFP embryonic stem cell co-cultured with the mouse preosteoblast cell line would differentiate into mature and functional motor neuron.

Example 4

OECs can Maintain the Ability of Self-Renewal of HB9::GFP$^+$

Figure 6:
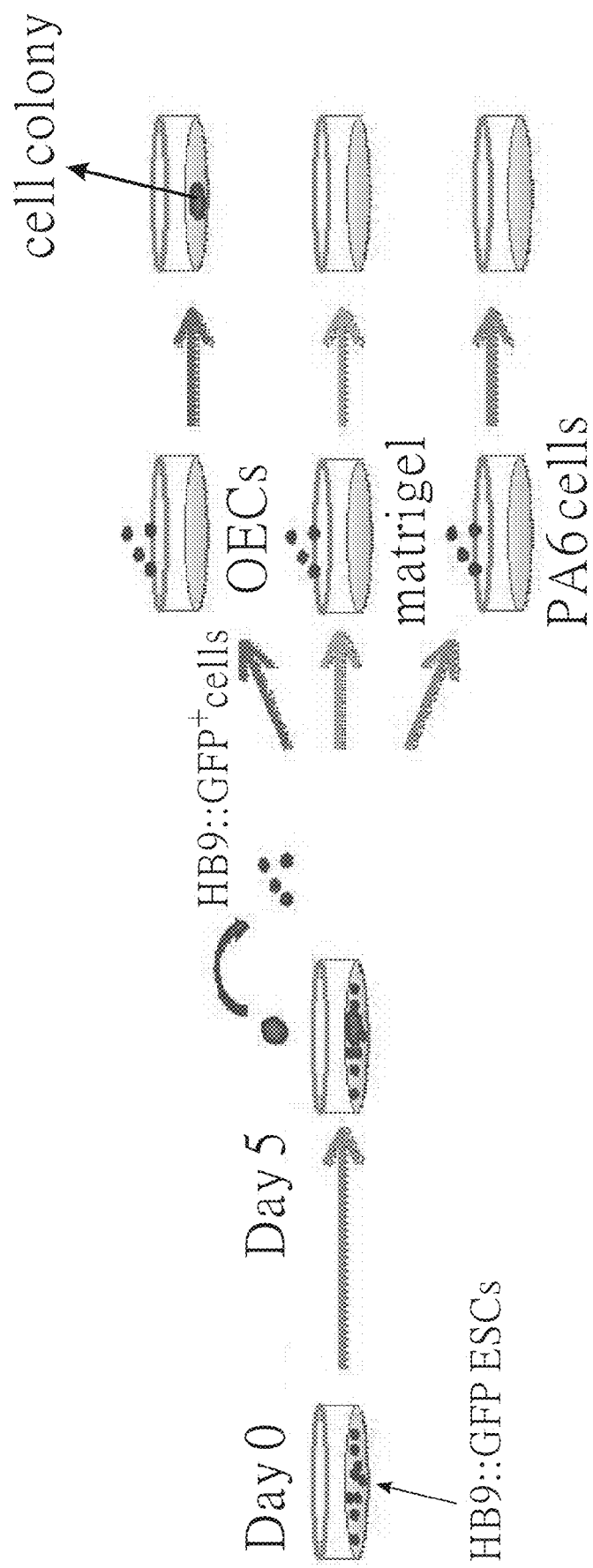
FIG. 6 shows the flow chart of HB9::GFP embryonic stem cells cultured under different conditions.

Please see FIG. 6. First of all, the HB9::GFP embryonic stem cells were cultured according the method disclosed in example 1 or 3 until the day 5. At the time, the green fluorescence just expressed at differentiated embryonic stem cell. The cell morphology of these green fluorescent cells was oval, without dendrites. Therefore, in this stage, the green fluorescent cells represented the progenitor cells of the motor neuron. And it was different with the mature motor neuron at the day 8.

At the day 5, a single green fluorescent HB9::GFP$^+$ cell was sorted by using the flow cytometer (Influx, nozzle 100 m, 25 psi, Becton-Dickinson). Then, it was cultured under a low-density condition of 100 cells/mL. Each single HB9:: GFP$^+$ was seeded on the OECs, PA6 cells and matrigel respectively for a week.

Figure 7:
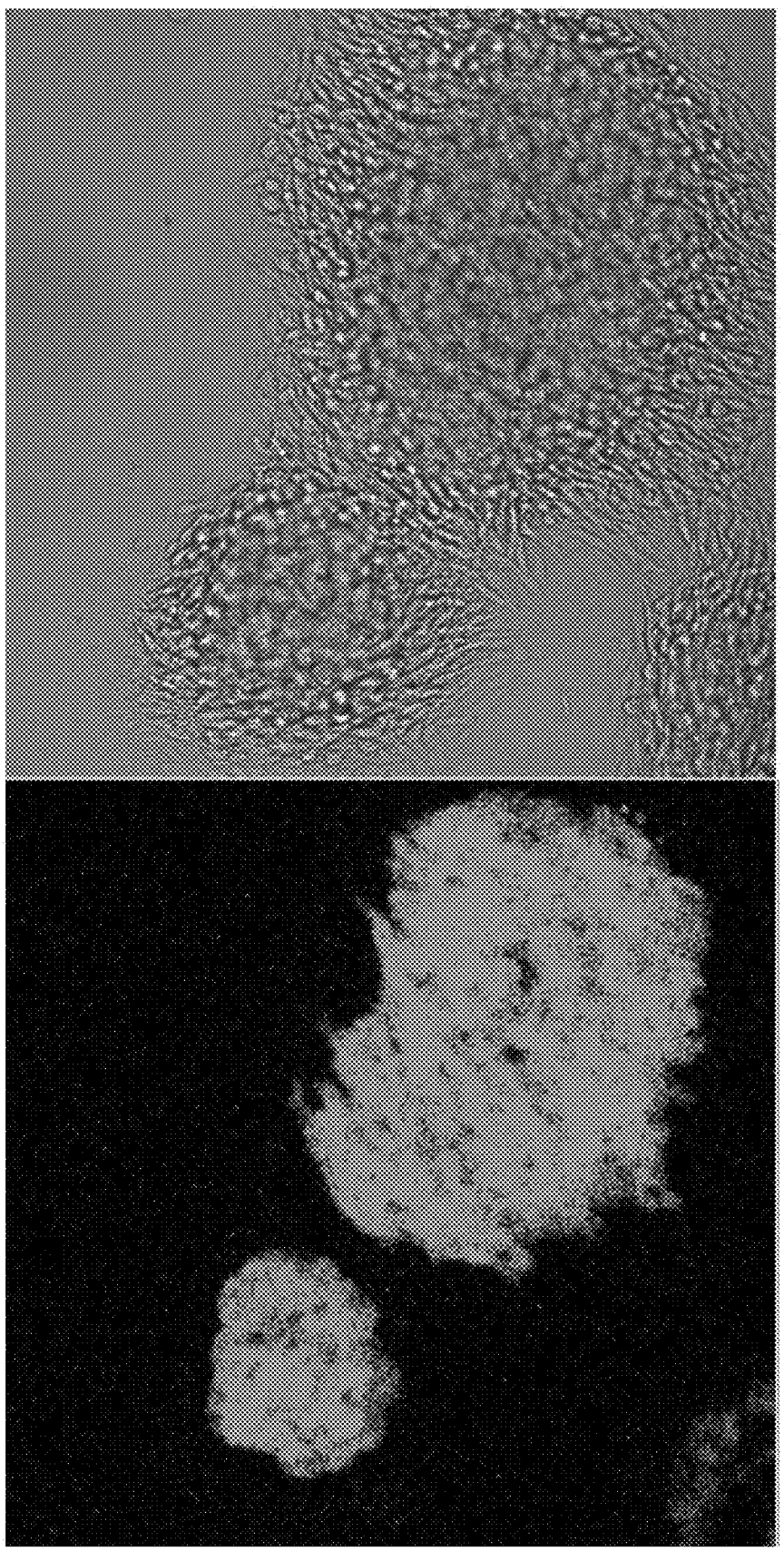
FIG. 7 shows single HB9::GFP+ cell seeded on the OECs for a week to form colonies.

Please see the FIG. 7. After one week culture, the HB9:: GFP$^+$ cell can only form a colony on the OECs, in contrast to the dispersed distribution of mature motor neurons on PA6 cells or matrigel. In addition, the HB9::GFP$^+$ cell can be passaged on OECs for over 10 times without loss of the GFP expression. It indicated that OECs provide specific niches to maintain the self-renewal of motoneuron progenitor cells.

Figure 8:
FIG. 8 shows single HB9::GFP+ cell seeded on the OECs pre-treated by mitomycin for a week to form colonies.
Figure 8:
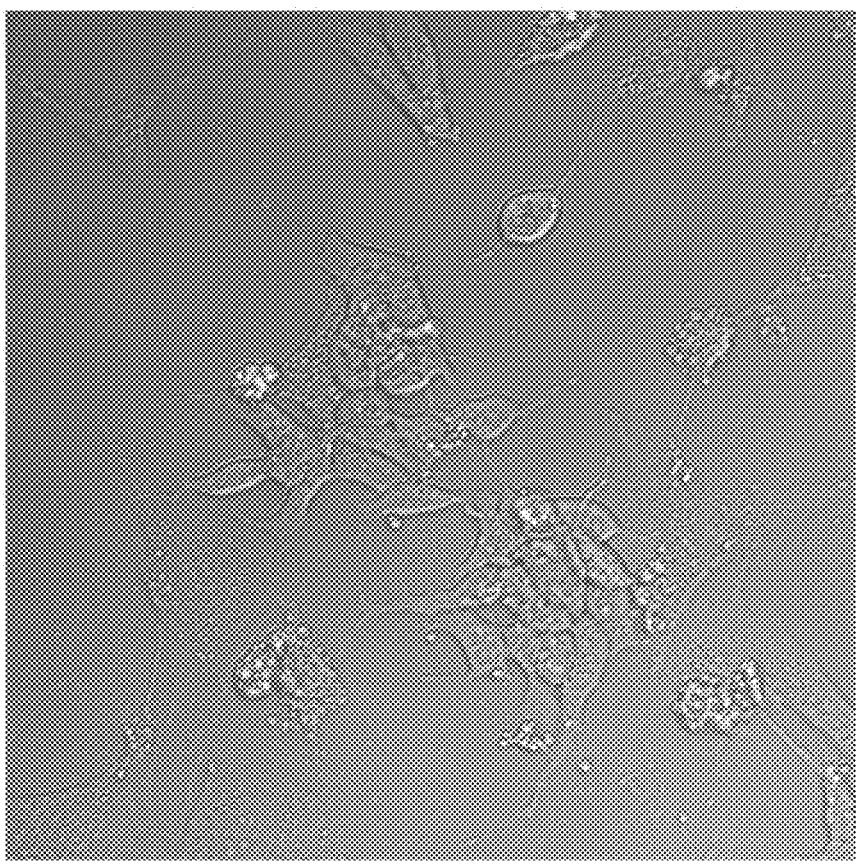

Furthermore, the sorted single HB9::GFP$^+$ cell was inoculated on the mitomycin-inactivated OECs for a week. The result was shown as FIG. 8. It shows that the mitomycin-inactivated OECs highly reduced the proliferation efficiency of HB9::GFP$^+$ cells and the proliferative HB9::GFP$^+$ cells cannot be maintained in the condition medium of OECs for over 5 passages.

Besides, the sorted single HB9::GFP$^+$ cell was cultured under high density condition of 10000 cells/mL and co-cultured for two weeks with the conditional media cultured for one day with the OECs but with no contact, and the culture solution was changed every two days. Under this culture condition, the single HB9::GFP$^+$ cell still can form a cell colony, renewal and subculture without contact with the OECs.

The foresaid results indicated that the co-culture with the healthy OECs or the conditional culture media had been cultured the OECs can provide the niches for sustaining the self-renewal of the motor neuron progenitor cell and to be an important environment factor for maintaining the HB9::GFP$^+$ cells.

Example 5

The Differentiation Potency of the Motor Neuron

Figure 9:
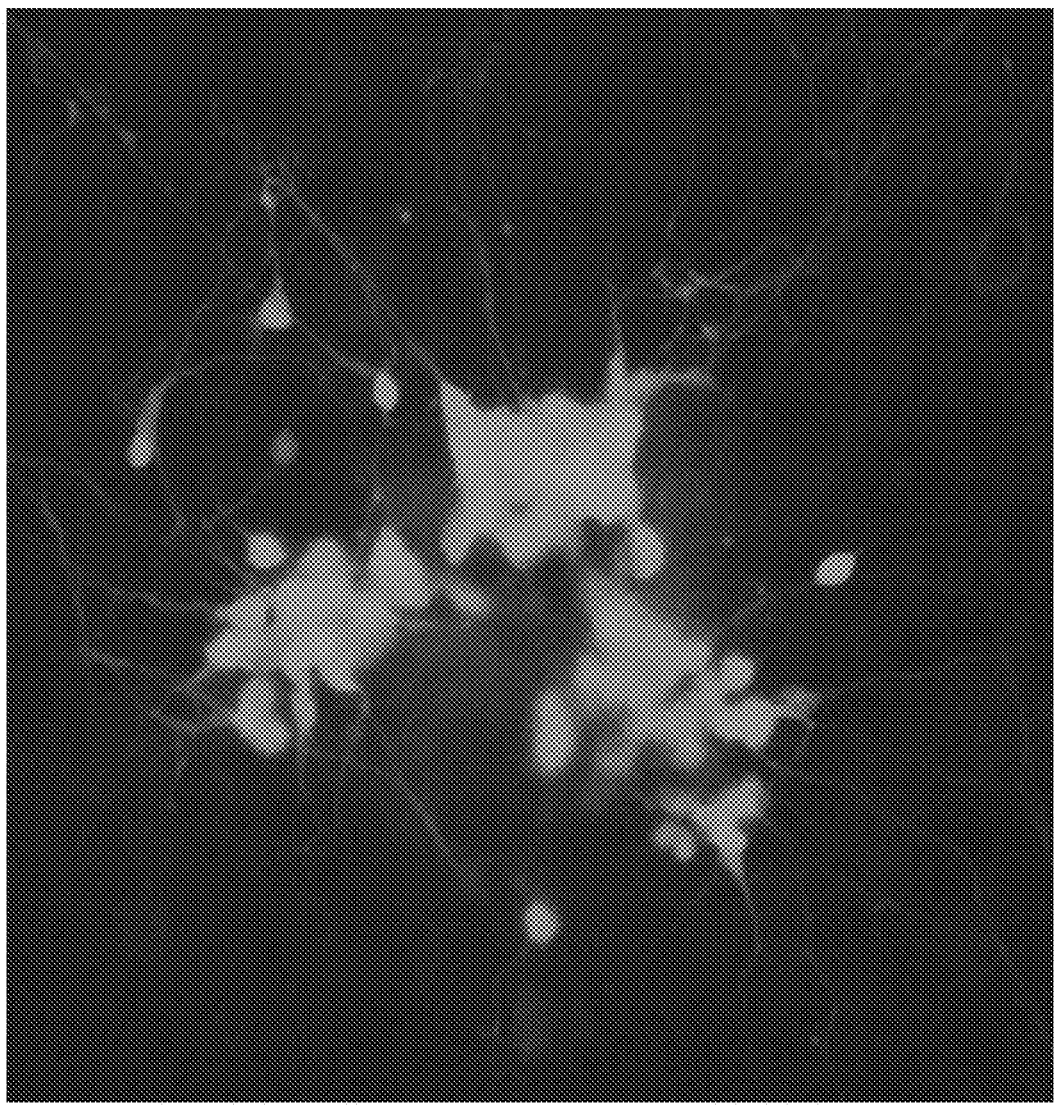
FIG. 9 shows the result of the HB9::GFP+ cell expanded on the OECs and then cultured on the PA6 cells.
Figure 10A:
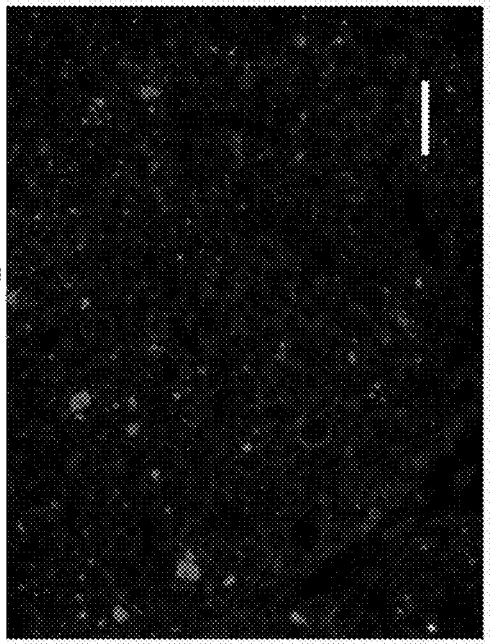
FIG. 10A shows the result of the expression level of CD11b in each group of rats by immunohistological staining method.
Figure 10A:
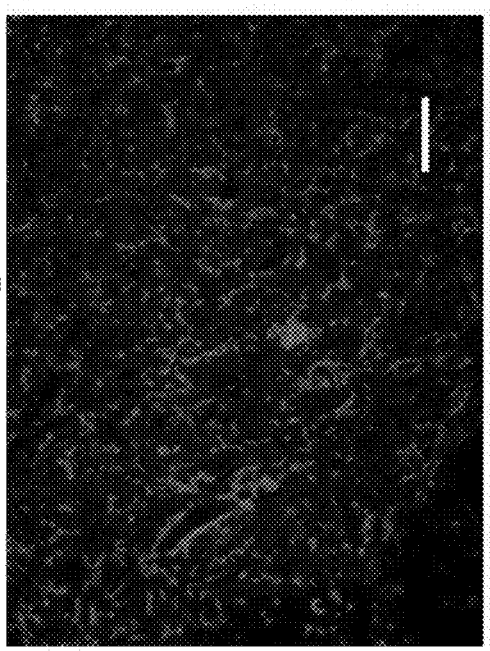
Figure 10A:
Figure 10A:
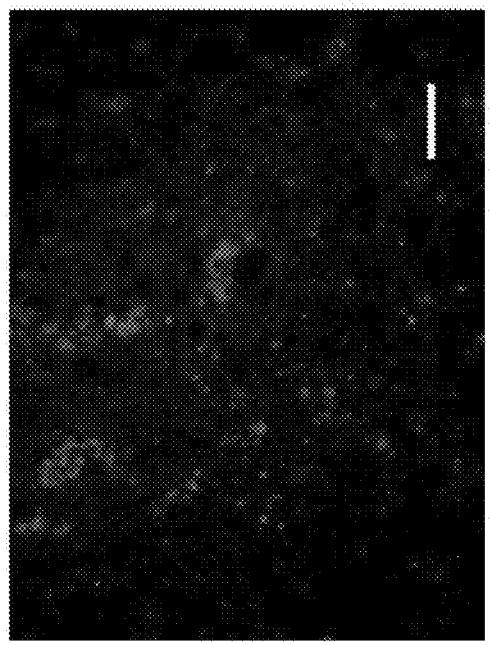
Figure 10B:
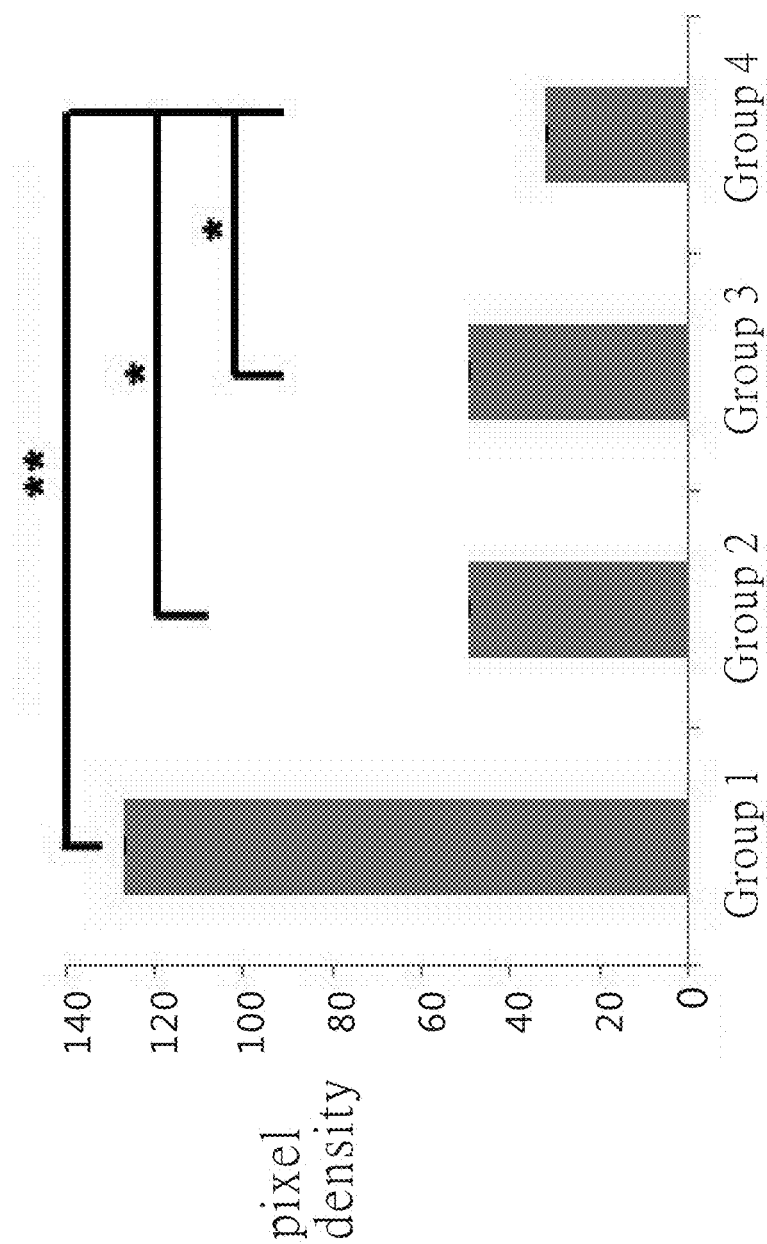
FIG. 10B shows the static result of the expression level of CD11b in each group of rats, wherein "*" means "P<0.05", "**" means "P<0.01".
Figure 11A:
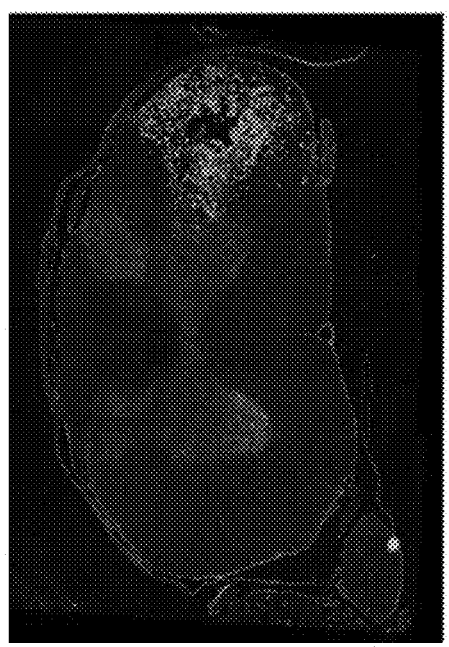
FIG. 11A shows the result of the expression level of choline acetyltransferase (CHAT) from motor neuron in each group of rats by immunohistological staining method.
Figure 11A:
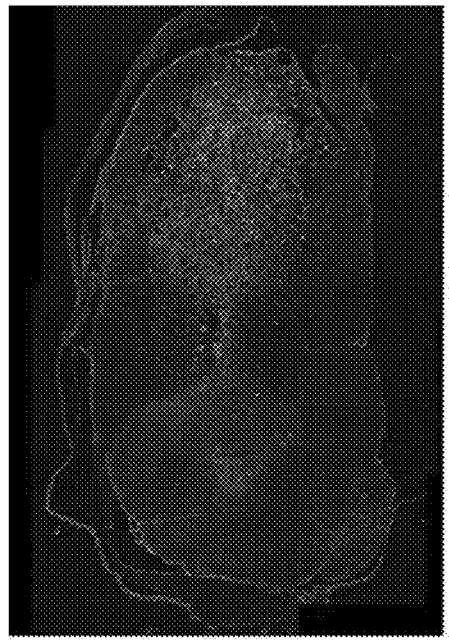
Figure 11A:
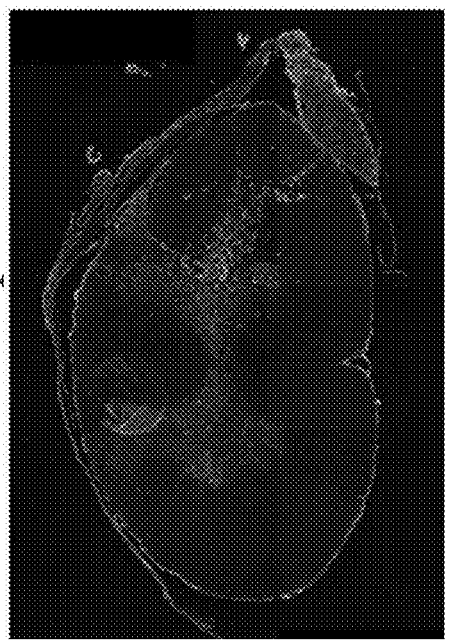
Figure 11A:
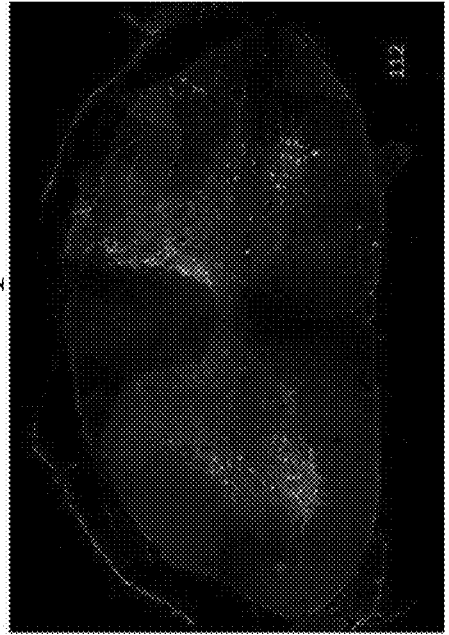
Figure 11B:
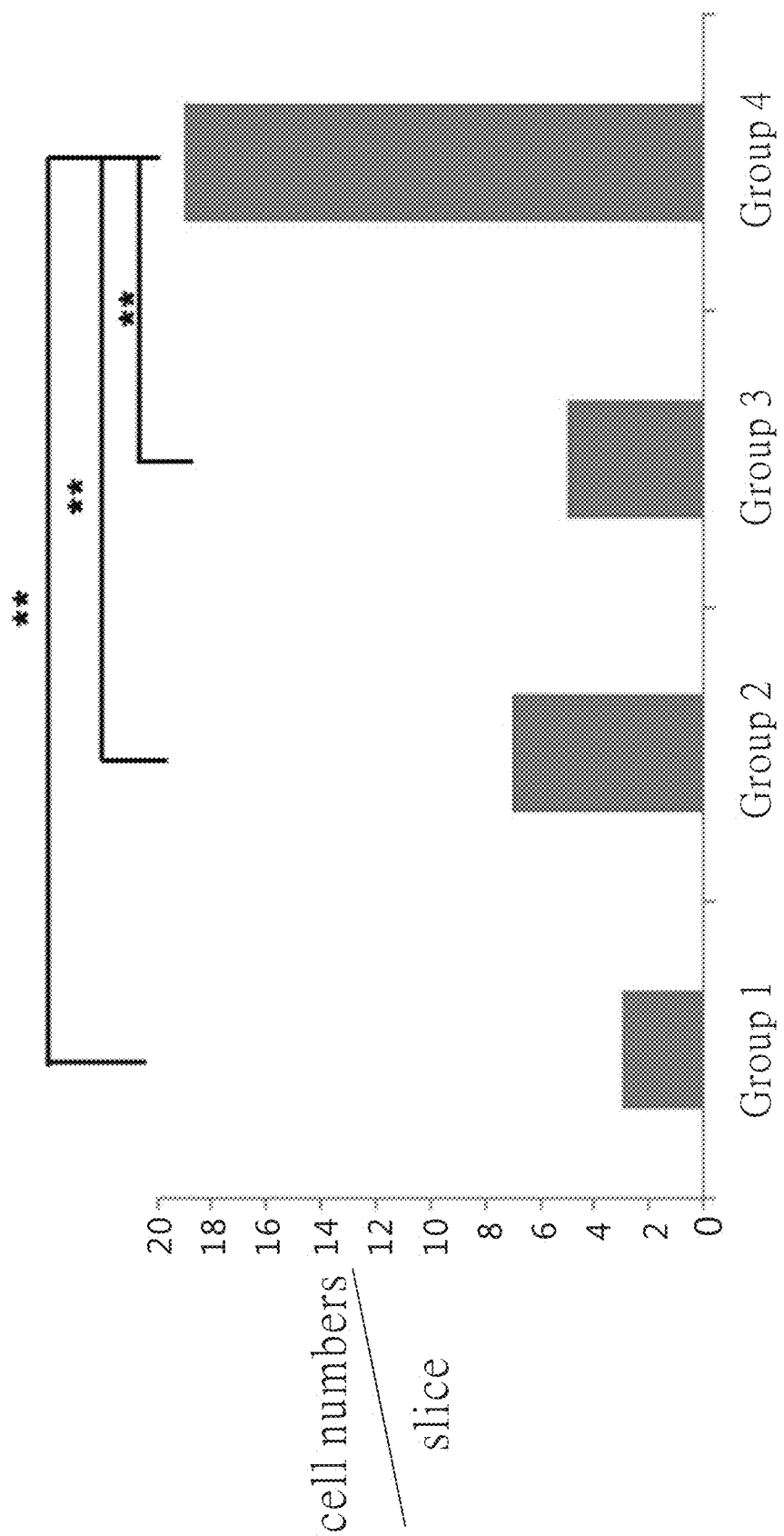
FIG. 11B shows the static result of the expression level of choline acetyltransferase from motor neuron in each group of rats, wherein "*" means "P<0.05", "**" means "P<0.01".

The pure HB9::GFP$^+$ cells from the OEC coculture system on passage 5 were sorted by using the flow cytometer (Influx, nozzle 100 m, 25 psi, Becton-Dickinson). The sorted HB9::GFP$^+$ cells were seeded on the PA6 cells for 3 days. Most sorted cells rapidly extended axons to become mature motor neurons and exhibited typical differentiated motor neuron conformation as the FIG. 9. As shown in FIG. 9, the expanded HB9::GFP$^+$ cells still maintain the differentiation potency and were able to differentiate into the mature motor neurons.

Example 6

Preparing Animal Model of Spinal Cord Injury

The method for preparing animal model of spinal cord injury in this example referred to prior references (Cheng F C, et al., 2012; Cheng F C et al., 2010; Yang D Y et al., 2012).

The SD rat weighing from 250-300 g were anesthetized with 4% isoflurane in induction followed by maintenance of 1-2% isoflurane. Right brachial plexus was approached through a horizontal incision parallel to clavicle running from sternum to the axillary region. The subclavian vessels were located and the lower trunk was dissected. The C7 root was grasped with forceps and extracted from the spinal cord for 5 minutes. Then the cut was sutured.

Example 7

Animal Test

The spinal cord injury rats prepared in example 6 were divided into 4 groups. After spinal cord injury for 2 weeks, a total laminectomy was performed in each rat on vertebrate T7-T8. Total 5×10$^5$ Cells were engrafted into the injured ventral horn and the contralateral intact regions. The group 1 was treated phosphate-buffered solution only. The group 2 was engrafted the OECs for 5×10$^5$ cells. The group 3 was engrafted the HB9::GFP$^+$ cells for 5×10$^5$ cells. The group 4 was engrafted the HB9::GFP$^+$ cells for 2.5×10$^5$ cells and the OECs for 2.5×10$^5$ cells, wherein the HB9::GFP$^+$ cells were pre-treated with the OECs for one day to stimulate the cell-renewal of the HB9::GFP$^+$ cells before engrafting.

The cell transplantation was performed by microinjection. Right side microinjections of the 2 µl cells/PBS into white mater was made at the coordinate of 0.75 mm from the midline and depth of 1.2 mm at of the spinal level of T8 and T9 using the infusion pump for 20 minutes and kept for 5 minutes after the termination of injection. Left side microinjections of 2 µl cells/PBS into anterior horn was made at the coordinate of 0.5 mm from the midline and depth of 1.2 mm at of the same spinal levels and procedures. After one week, each group of rats was anesthetized and transcardially perfused with 25 mL phosphate-buffered solution followed by 100 ml of 4% paraformaldehyde. Each of their spinal cords was taken for immunohistochemistry staining to observe the expression level of CD11b, choline acetyltransferase. The results were shown as FIGS. 10 and 11.

Because the microglial cells of spinal cord injury rat were over-active, it induced the inflammatory of neural cells. The microglial cells would largely express the CD11b and damage the motor neurons. The result from FIGS. 10 and 11 indicated that the expression level of the CD11b from the rat of the group 1 was significantly higher than other groups. And the motor neurons from the anterior horn of the spinal cord which were labeled by choline acetyltransferase showed that the motor neurons from the rat of the group 1 suffered a severe damage. Compared with the rat of the group 1, the expression level of the CD11b from the rat of the group 4 was significantly lower. And a lot of motor neurons in the group 4 expressed the choline acetyltransferase. It showed that most of its endogenetic motor neuron were not damaged. Further compared with the rat of the group 4 and the group 2 or 3, it could understand that co-transplantation of the motor neuron and OECs was more effective for the repairing of motor neurons on subject than only transplantation of the motor neuron or OECs.

From the results of foresaid examples, it shows that the method of continuously maintaining the activity of the motor neuron progenitor cell can actually keep the ability to self-renewal under the environment of the appearance of health OECs, so it can provide more significant protection than prior art for the motor neuron. And the motor neuron progenitor cells produced from the process of culture under the condition of differentiation can still differentiate into the mature motor neuron to help the growth of motor neuron and the reconstruction of nerve function. According to the foresaid method, this invention can provide a pharmaceutical composition and treatment to transplant the motor neuron progenitor cells having the ability to self-replicate and differentiate into a subject to make the motor neuron progenitor cells replicate in advanced, then to repair or recover the damage part of nerve in the subject to achieve the effect of significantly treating the diseases of motor neuron.

The above-mentioned detailed description and specific examples are given for illustration of this present invention only. Any easy changes or modifications base on examples in the description by the person skilled in the art of this present invention will be included within the scope of following claims.

What is claimed is:

1. A method for continuously maintaining growth of a motor neuron progenitor cell, comprising:
    culturing a motor neuron progenitor cell under a plurality of culture mediums sequentially to make the motor neuron progenitor cell maintain the ability to self-renew and differentiate to a mature motor neuron cell,
    wherein the plurality of culture mediums comprising a first culture medium, a second culture medium, a third culture medium and a fourth culture medium, the first culture medium contains 10% knockout serum replacement, the second culture medium contains knockout serum replacement and retinoic acid, the third culture medium is neurobasal media containing retinoic acid and purmorphamine for co-culturing, the fourth culture medium is neurobasal media,
    wherein the motor neuron progenitor cell is cultured in the first culture medium on the first to the third day, in the second medium on the third to fifth day, in the third medium on the fifth to seventh days under a low-density condition of 100 cells/mL, and in the fourth culture medium until the eighth day,
    wherein the motor neuron progenitor cell is cultured in the fourth culture medium comprising an olfactory ensheathing cell under a low-density condition of 100 cells/mL.

2. The method for continuously maintaining growth of a motor neuron progenitor cell according to claim 1, wherein at least one motor neuron progenitor cell is seeded on the olfactory ensheathing cell.

3. The method for continuously maintaining growth of a motor neuron progenitor cell according to claim 1, wherein the single motor neuron progenitor cell has ability to form a colony under the culture condition.

4. A method for continuously maintaining growth of a motor neuron progenitor cell, comprising:
    culturing a motor neuron progenitor cell under a plurality of culture mediums sequentially to make the motor neuron progenitor cell maintain the ability to self-renew and differentiate to a mature motor neuron cell,
    wherein the plurality of culture mediums comprising a first culture medium, a second culture medium, a third culture medium and a fourth culture medium, the first culture medium contains 10% knockout serum replacement, the second culture medium contains knockout serum replacement and retinoic acid, the third culture medium is neurobasal media containing retinoic acid and purmorphamine for co-culturing, the fourth culture medium is neurobasal media,
    wherein the motor neuron progenitor cell is cultured in the first culture medium on the first to the third day, in the second medium on the third to fifth day, in the third medium on the fifth to seventh days under a low-density condition of 100 cells/mL, and in the fourth culture medium until the eighth day,
    wherein the motor neuron progenitor cell is cultured in the fourth culture medium pre-treated with the olfactory ensheathing cell under high density condition of 10000 cells/ml and then the olfactory ensheathing cell is removed.

* * * * *